United States Patent [19]
Hunkapiller et al.

[11] Patent Number: 4,811,218
[45] Date of Patent: Mar. 7, 1989

[54] REAL TIME SCANNING ELECTROPHORESIS APPARATUS FOR DNA SEQUENCING

[75] Inventors: Michael W. Hunkapiller, San Carlos; Charles R. Connell, Redwood City; William J. Mordan, Sunnyvale; John D. Lytle, San Jose; John A. Bridgham, Hillsborough, all of Calif.

[73] Assignee: Applied Biosystems, Inc., Foster City, Calif.

[21] Appl. No.: 869,421

[22] Filed: Jun. 2, 1986

[51] Int. Cl.$^4$ .......................... G01N 27/26; C12Q 1/68
[52] U.S. Cl. .......................... 364/413.01; 204/299 R; 435/6; 935/77; 935/87
[58] Field of Search ................ 435/6; 204/299 R; 935/87, 77; 364/413

[56] References Cited

U.S. PATENT DOCUMENTS

| | | | |
|---|---|---|---|
| 4,130,824 | 12/1978 | Amos et al. | 346/33 A |
| 4,329,591 | 5/1982 | Fujiwara et al. | 250/548 |
| 4,675,095 | 6/1987 | Kambara et al. | 204/299 R |
| 4,707,235 | 11/1987 | Englert et al. | 204/299 R X |

FOREIGN PATENT DOCUMENTS

| | | |
|---|---|---|
| 0157280 | 10/1985 | European Pat. Off. |
| 0214713 | 3/1987 | European Pat. Off. |
| 2417305 | 10/1974 | Fed. Rep. of Germany |
| 3020729 | 12/1980 | Fed. Rep. of Germany |
| 3620235 | 12/1986 | Fed. Rep. of Germany |
| 2558262 | 1/1985 | France |
| 2155176 | 9/1985 | United Kingdom |
| 2180941 | 4/1987 | United Kingdom |

OTHER PUBLICATIONS

Smith, L. M. et al. "Fluorescence Detection in Automated DNA Sequence Analysis", Nature, Jun. 12, 1986, 674–678.
Kanbara, Hideki, Hitach LTD., "Gel Electrophoretic Apparatus", 7/18/86 Patent Abstracts of Japan vol. 10 P478, 61–47549.
Zoler, Mitchel L., "Caltech Develops New DNA Sequencing Method", Bio/Technology vol. 3 May 1985, pp. 395–396.

Primary Examiner—Jerry Smith
Assistant Examiner—Clark A. Jablon
Attorney, Agent, or Firm—Joseph H. Smith

[57] ABSTRACT

A real-time, automated, nucleic acid sequencing apparatus that offers high speed, definitive sequencing on many samples at the same time. The apparatus permits more than one clone to be sequenced at a time, thus vastly decreasing the time required to sequence longer fragments and reducing sequencing costs accordingly. The apparatus detects electromagnetic radiation from a plurality of lanes in an electrophoresis system wherein the plurality of lanes are arranged in a planar array. The apparatus includes an optical system for detecting the radiation at a plurality of wavelengths and is made up of a collection element, a filter for selectively transmitting the plurality of wavelengths received from the collection element, and a detection system for measuring intensity of the radiation received from the filter means. A translational stage is used for mounting the optical system and for moving the optical system parallel to the planar array in order to move the collection element back and forth across the lanes in order to receive radiation from the lanes, one lane at a time during electrophoresis. Also included is a computer system for controlling the filter and the stage, and for receiving intensity data from the detector and correlating that data with the corresponding lane and corresponding wavelengths transmitted by the filter in substantially real time.

14 Claims, 14 Drawing Sheets

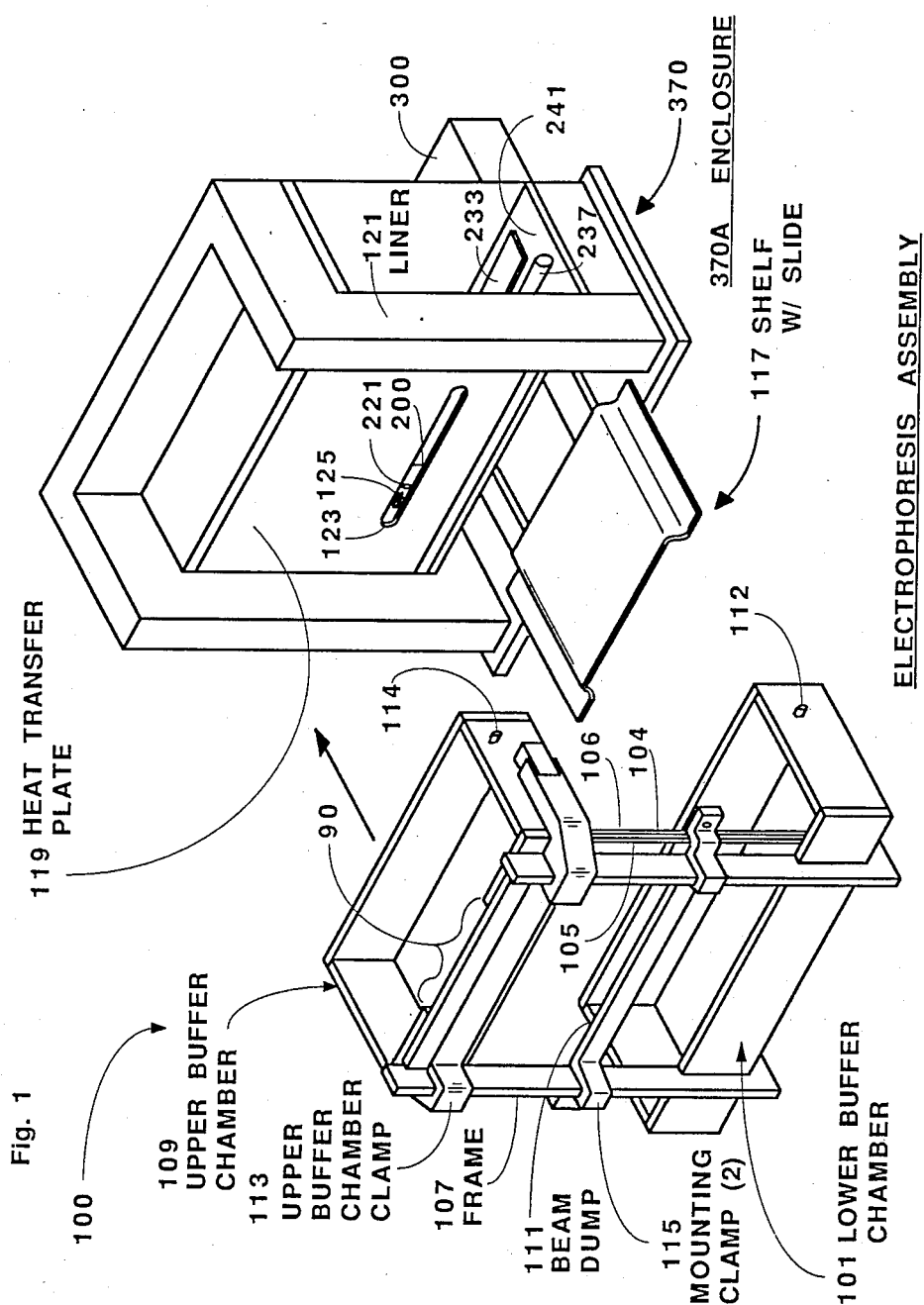

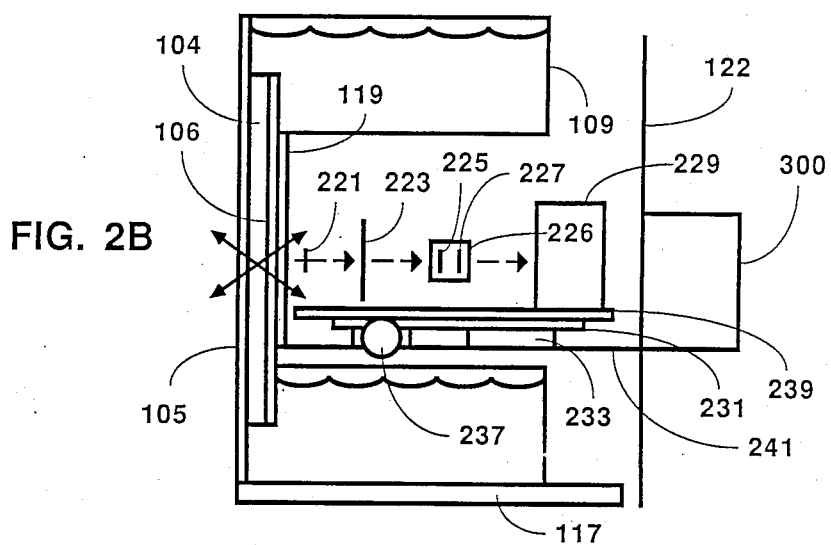
FIG. 2B
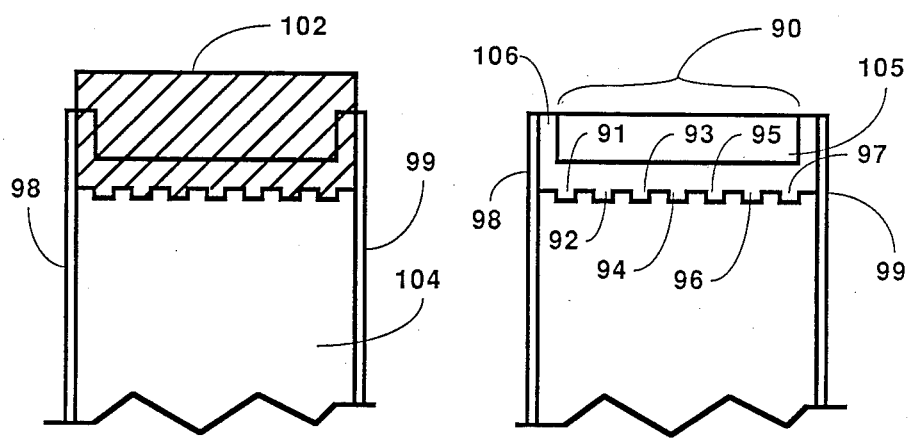
FIG. 3A
FIG. 3B

SIDE A:
C.A. DIA. = 7 mm.

SIDE B
FLAT: ± 2 Fr
C.A. DIA. = 7 mm.

MATERIAL - SCHOTT BK7
GRADE B (OR EQUIV.)

AXIAL THICKNESS = 2.00 ± .1

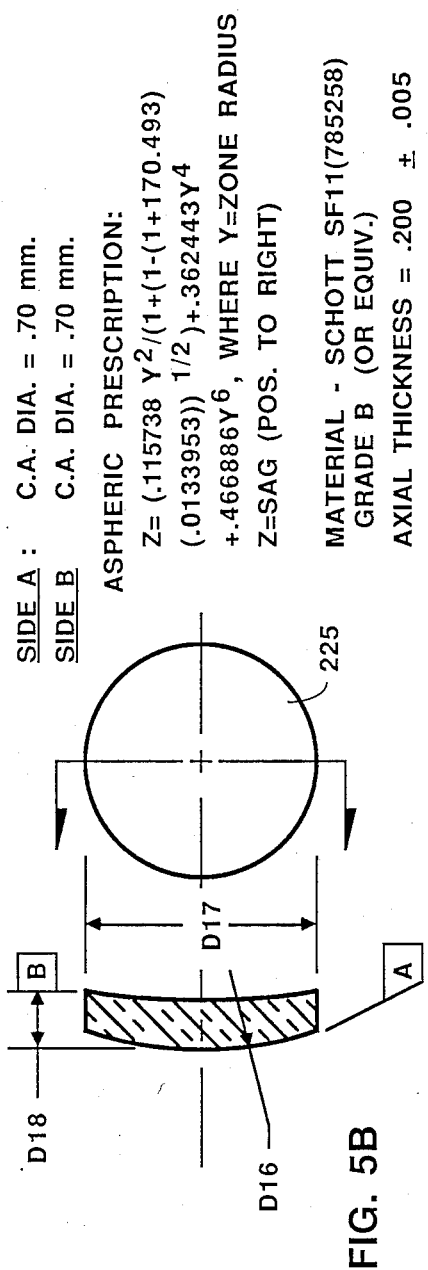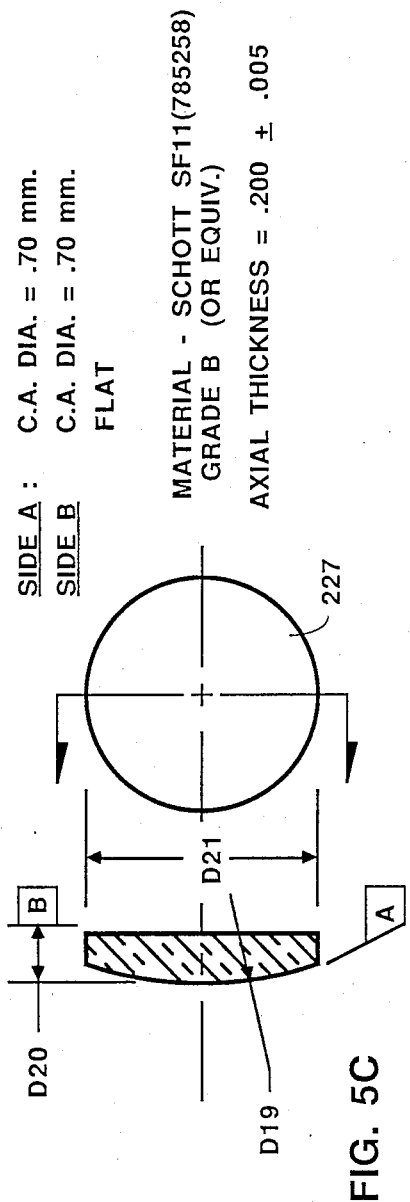
FIG. 5B
FIG. 5C

SIDE A: C.A. DIA. = 13.2 mm - FLAT
SIDE B  C.A. DIA. = 15.0 mm.

ASPHERIC PRESCRIPTION:
SAG Z = $-1.1235722 \times 10^{-1} Y^2 / (1 + (1 - (1 + .770942)(1.1235722 \times 10^{-1})^2 Y^2)^{1/2}) - 1.76995 \times 10^{-5} Y^4 + 1.35791 \times 10^{-7} Y^6 - 3.09867 \times 10^{-10} Y^8 + 7.52363 \times 10^{-12} Y^{10}$

MATERIAL - SCHOTT SF11(785258) GRADE B (OR EQUIV.)
AXIAL THICKNESS = .200 ± .005

FIG. 6
TABLE (DIMENSIONS NOT LABELED ARE MILLIMETERS)

$$
\begin{aligned}
A &= 15.5 \text{ DEGREES} \\
B &= 33 \text{ DEGREES} \\
D1 &= .456 \text{ in.} \\
D3 &= .670 \text{ in.} \\
D4 &= 1.037 \text{ in.} \\
D5 &= 2.0 \pm .1 \\
D6 &= 26.5 \pm .05 \\
D7 &= 10.00 + 0, - .02 \\
D8 &= 7.58 \pm .05 \\
D9 &= 8.0 \pm .1 \\
D10 &= 10.00 + 0, - .02 \\
D11 &= 19.8 \pm .1 \\
D12 &= .357 \text{ in.} \\
D13 &= 3.900 \text{ in.} \\
D14 &= .500 \text{ in.} \\
D15 &= .088 \text{ in.} \\
D16 &= 1.12 \pm .01 \\
D17 &= 0.800 + .000, - .005 \\
D18 &= .200 \pm .005 \\
D19 &= .666 \pm .005 \\
D20 &= .200 \pm .005 \\
D21 &= 0.800 + .000, - .005 \\
D22 &= 6.00 \pm .2 \\
D23 &= 16.00 + .00, - .02 \\
D24 &= .270 \text{ in.}
\end{aligned}
$$

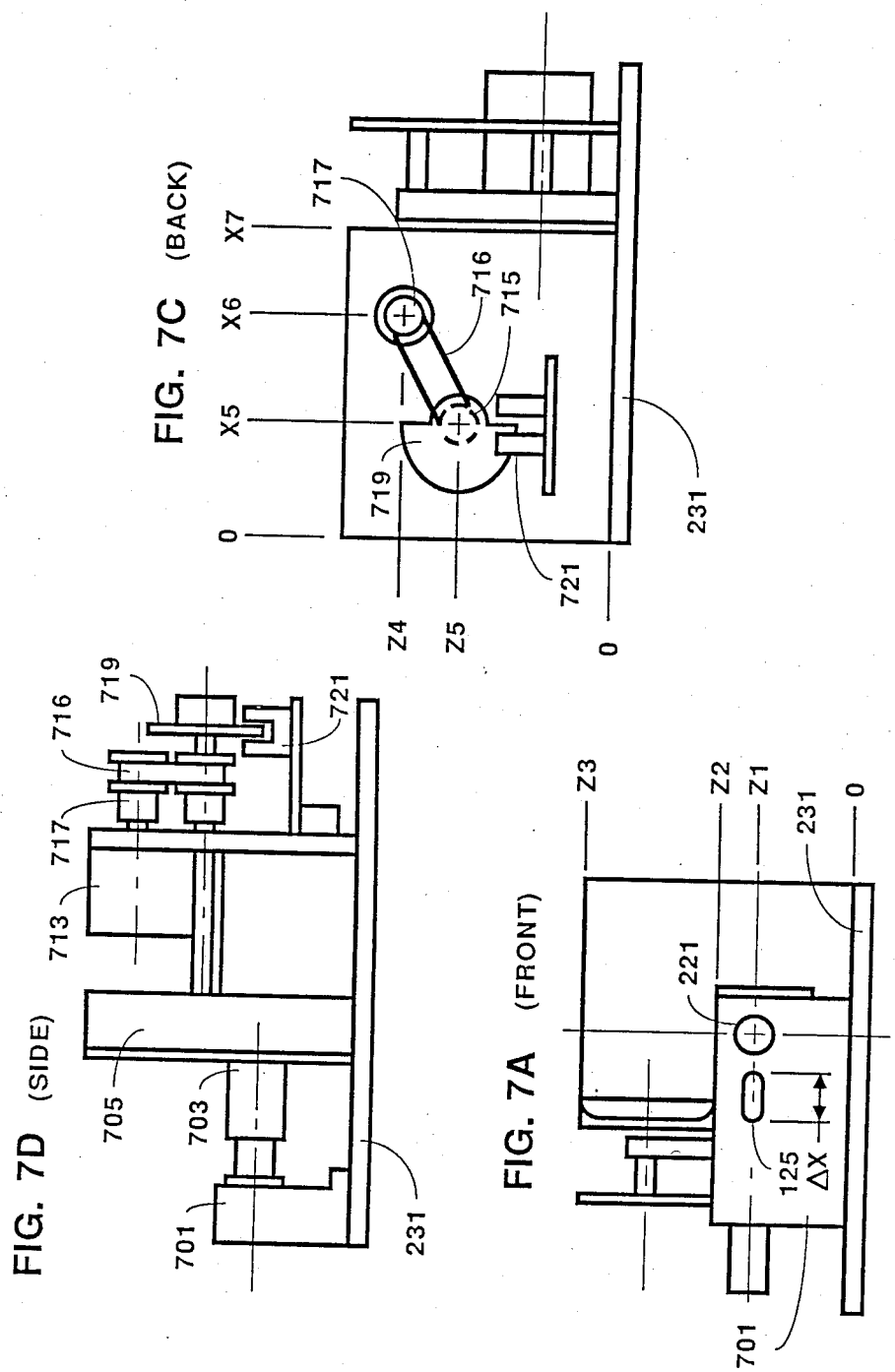

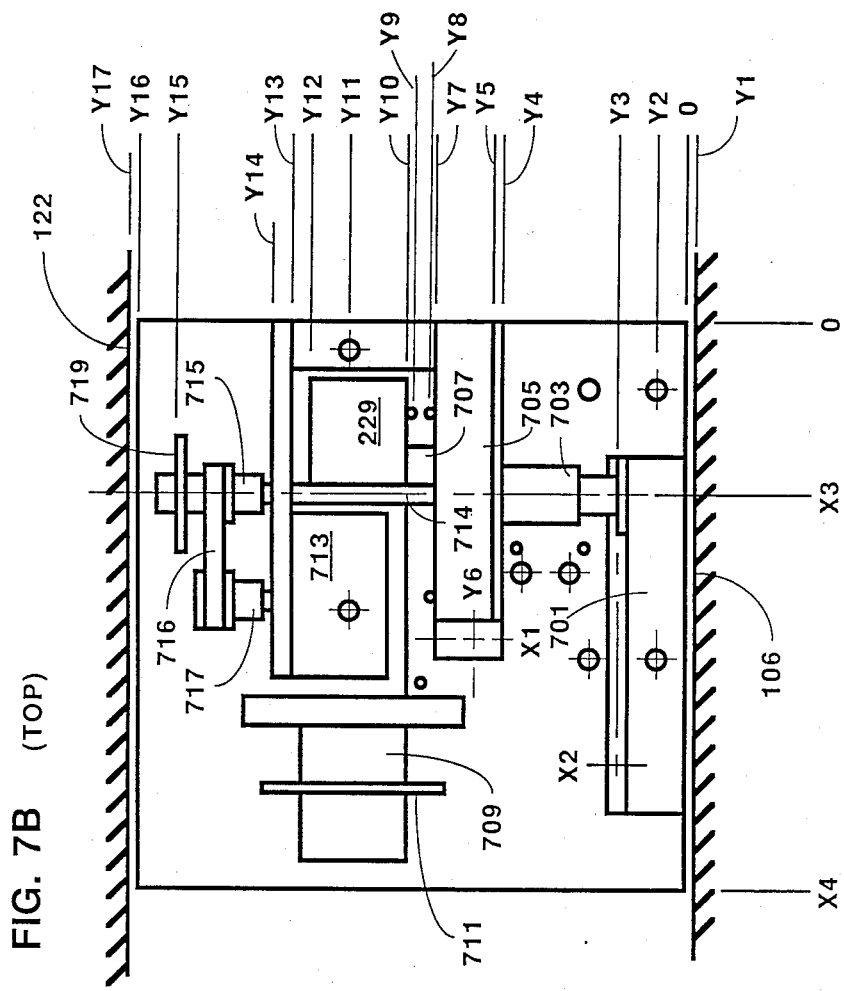
FIG. 7B (TOP)

FIG. 7E
TABLE (All Dimensions In Inches)

$\Delta X$ = 0.25
X1 = 3.656
X2 = 5.000
X3 = 1.750
X4 = 6.000
X5 = 1.750
X6 = 2.906
X7 = 3.937

Y1 = -.260
Y2 = .375
Y3 = .843
Y4 = 3.250
Y5 = 3.312
Y6 = 3.687
Y7 = 4.002
Y8 = 4.125
Y9 = 4.437
Y10 = 4.500
Y11 = 5.250
Y12 = 6.000
Y13 = 6.125
Y14 = 6.312
Y15 = 7.062
Y16 = 7.312
Y17 = 7.865
Z1 = 1.250
Z2 = 2.000
Z3 = 4.125
Z4 = 3.093
Z5 = 2.125

Monitor Color

Green = A ( 2', 7' - dimethoxy - 4', 5' - dichlorofluorescein )
Blue = C ( fluorescein - 5 - isothiocyanate )
Red = T ( Texas Red)
Black = G ( tetramethylrhodamine - 5 - isothiocyanate )

REAL TIME SCANNING ELECTROPHORESIS APPARATUS FOR DNA SEQUENCING

BACKGROUND OF THE INVENTION

This invention pertains to apparatus for fluorescence detection in electrophoresis systems, and particularly to such apparatus for automatic sequencing of nucleic acids.

The structural analysis of DNA plays an increasingly important role in modern molecular biology. About $4 \times 10^6$ bases of DNA have been sequenced since the introduction of the enzymatic, or dideoxy, method of rapid sequencing developed by Sanger and his coworkers (Sanger, et al, Proc. Natn. Acad. Sci. U.S.A. 74,5463–5467 (1977), A. J. H. Smith, Meth. Enzymol. 65,560–580 (1980)) and the chemical method developed by Maxam and Gilbert (S. M. Maxam and W. Gilbert, Meth. Enzymol. 65,499–559 (1980)). Typically, four separate reactions are performed on the particular DNA segment to be analyzed. In the enzymatic method, these reactions produce DNA fragments terminating in either adenosine (A), cytosine (C), quanosine (G), or thymidine (T). In the chemcial method, typically, fragments terminating in G, G+A, C+T, or C are produced. In both cases the four sets of reaction products are electrophoresed in adjacent lanes of a high-resolution polyacrylamide gel. An autoradiographic image of the gel is produced, and the autoradiogram is examined to determine the relative lengths of the DNA fragments generated in each of the four reactions. The DNA sequence is inferred directly from that information.

Both of these techniques are very effective but they are also highly labor-intensive, relatively expensive, and involve the use of radioisotopes; values of approximately three to ten thousand bases sequenced per person-year at a cost of one to five dollars per base are representative. For these reasons and since much DNA remains to be sequenced (there are $3 \times 10^9$ bases in the human genome alone), there has been much recent activity directed toward development of an automated and non-isotopic method of DNA sequence analysis.

One of the more successful attempts has been carried out by Lloyd Smith and coworkers in the laboratory of Leroy Hood at California Institute of Technology (see Bio/Technology, Vol. 3, May 1985). In that approach, four fluorescent dyes with different colored tags are used instead of radioactive labels. Each color corresponds to a different nucleoside so that if the samples are co-separated electrophoretically, the "ladder" of DNA fragments produced during sequencing is segregated into fluorescent multi-colored rungs, each color corresponding to one of the bases A, G, C, or T. As the length of the column is scanned by a fluorescence sensor, the order of the colored bands corresponds to the specific gene sequence. The specific fluorophores selected by Smith, et al, were fluorescein isothiocyanate (FITC) with an emission peak at 520 nm, 4-chloro-7-nitrobenzo-2-oxa-1-diazole (NBD chloride) emitting at 550 nm, tetramethylrhodamine isothiocyanate (TMRITC) emitting at 580 nm, and Texas Red emitting at 610 nm. These emission peaks make the dyes look green, green-yellow, orange-red, and red, respectively.

The specific method used by Smith, et al, was an adaptation of the dideoxy (enzymatic) method of Sanger, which generally involves cloning the gene of interest in the single-stranded DNA phage M13. A primer sequence complementary to the phase sequence adjacent to the cloned gene is used to initiate a DNA synthesis that copies a portion of the gene. In the scheme devised by the Cal Tech group, a single molecule of fluorescent label is linked to each primer. The cloned genes and primers are then placed in four separate DNA synthesis reaction mixtures, each containing all four nucleosides. A small amount of a dideoxy form of a nucleoside, ddATP, ddCTP, ddGTP, or ddTTP is added to each batch. When a dideoxy triphosphate randomly replaces a conventional nucleoside and is incorporated into the developing DNA strand in the synthesis reaction, the nascent DNA copy immediately stops growing. As a result, all strands in the batch with ddATP terminate at a location where adenosine appears in the sequence. Site-specific stops at the C, G, and T positions occur in the other three reaction batches as well.

To distinguish the four bases, a different fluorescent label is used in each reaction mixture. To achieve that, all DNA copies that end in A are labeled with the green-colored FITC; those terminating in C are labeled with the green-yellow NBD chloride, those terminating in G are labeled with the orange-red TMRITC tag, and copies terminating in T are labeled with Texas Red.

In the Cal Tech automated system, aliquots from all four reaction mixtures are electrophoresed through a single polyacrylamide tube gel that sorts the various length fragments by size. Positioned at the bottom of the electrophoresis gel is an argon ion laser that sequentially illuminates each band as it migrates through the gel. When excited by laser light the fluorophores emit at their characteristic wavelength, and the emissions are detected and identified by a sensor. The sequence of emission colors is converted by the machine into a nucleotide sequence.

Although the Cal Tech group has been able to automate the sequencing process, bringing what used to require four lanes into one lane, and have substantially eliminated problems with mobility differences between bases, significant problems still remain to be solved. First, the detection system design is less than optimal in sensitivity. Second, and more importantly, the apparatus can handle only one column at a time, whereas when using autoradiographs many lanes on a slab gel can be sequenced at the same time.

What is needed is a high throughput, real time, fluorescence detection apparatus that can perform nucleic acid sequencing on many lanes of a gel simultaneously. Furthermore, the apparatus should have a high sensitivity but the detection system should not require frequent attention by trained personnel.

SUMMARY OF THE INVENTION

A real-time, automated, nucleic acid sequencing apparatus is provided that offers high speed, definitive sequencing on many samples at the same time. The apparatus permits more than one clone to be sequenced at a time, thus vastly decreasing the time required to sequence longer fragments and reducing sequencing costs accordingly. Furthermore, the detection system at the heart of the apparatus is designed to eliminate costly alignment procedures and, concomitantly, to eliminate the need for constant attention by highly trained personnel.

In its broadest sense, and in accordance with preferred embodiments of the invention, an apparatus is provided for detecting electromagnetic radiation from a plurality of lanes in an electrophoresis system wherein the plurality of lanes are arranged in a planar array. The apparatus includes an optical system for detecting the radiation at a plurality of wavelengths emanating from the plurality of lanes. To accomplish that function, the optical system is made up of a collection for focussing the radiation, a filter for selectively transmitting the plurality of wavelengths received from the collection element, and a detection system for measuring intensity of the radiation received from the filter means. The apparatus also has a translational stage for mounting the optical system and for moving the optical system in a direction parallel to the planar array of electrophoresis lanes in order to move the collection element to receive radiation from the lanes, one lane at a time. The apparatus also includes a computer system for controlling the filter and the stage. The computer system also receives intensity data from the detector and correlates the intensity data with the corresponding lane and corresponding wavelengths transmitted by the filter in real time.

To use the apparatus for sequencing nucleic acids, the nucleic acids are prepared according to the enzymatic method and labeled as per Smith, et al. Nucleic acids are then electrophoresed in the apparatus and the computer is used to sort the intensity data into time and wavelength information for each lane, thereby arriving at a sequence for each lane.

BRIEF DESCRIPTION OF THE DRAWINGS

FIG. 1 illustrates an electrophoresis apparatus and enclosure according to the invention.

FIG. 2B is a schematic representation of the invention in a vertical cut through the optical system.

FIGS. 3A and 3B illustrate the construction of wells in the electrophoresis apparatus.

FIGS. 5B, 5C and 5D show details of the lenses illustrated in FIG. 5A.

FIG. 6 is a table showing detailed dimensions for the lenses and optical system.

FIGS. 7A–7D illustrate the mechanical configuration of the optical system in four views.

FIG. 7E is a table of dimensions for the mechanical configuration shown in FIGS. 7A–7D.

DETAILED DESCRIPTION OF THE INVENTION

Figure 2A:
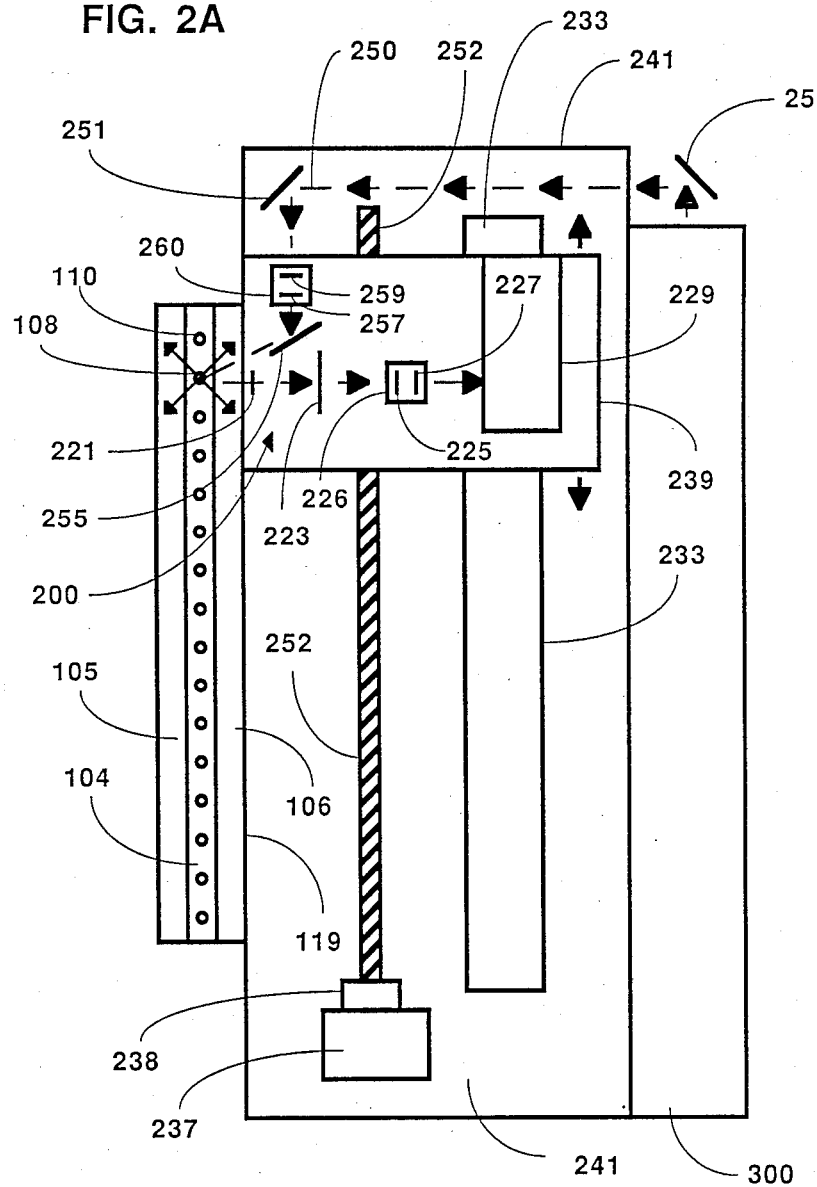
FIG. 2A shows a schematic representation of the invention in a horizontal cut through the optical system.
Figure 4A:
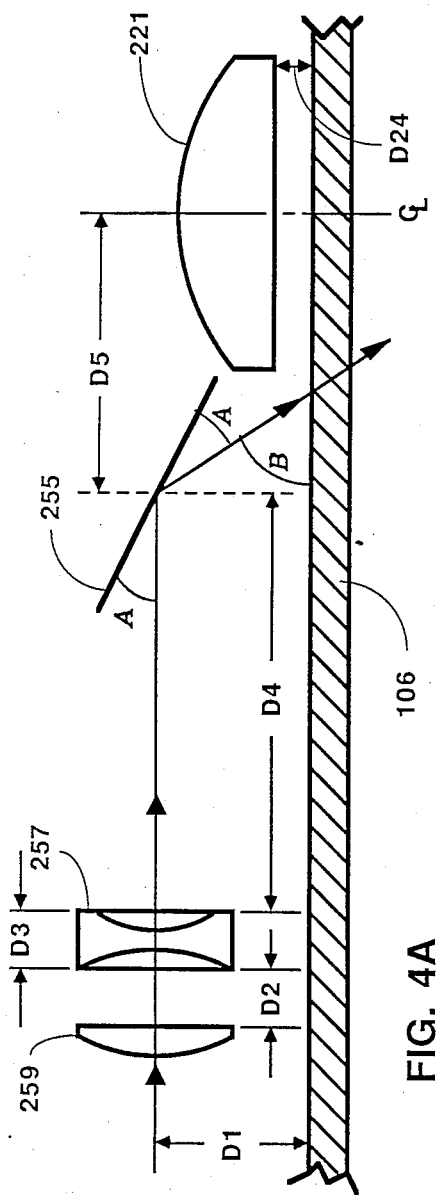
FIG. 4A illustrates a focussing telescope according to the invention.
Figure 4B:
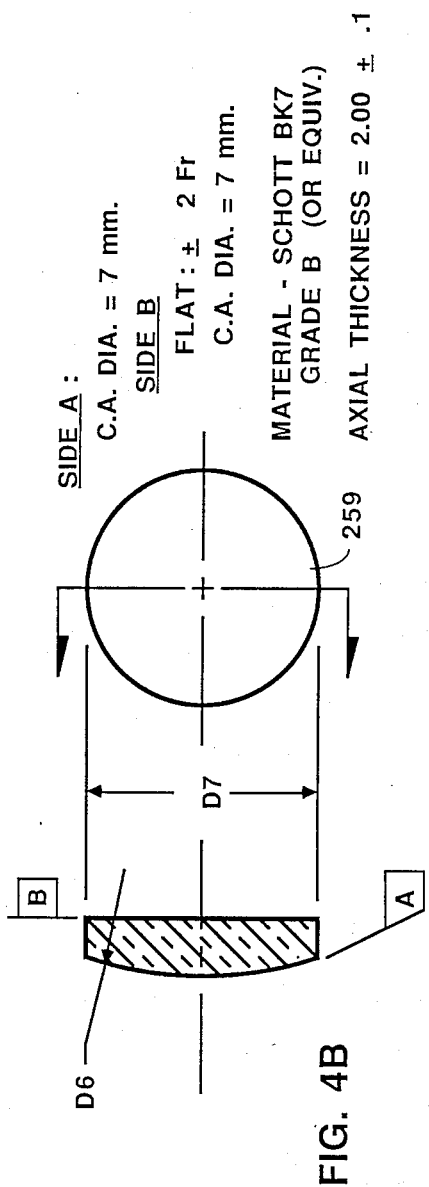
FIGS. 4B and 4C show details of lenses used in the focussing telescope.
Figure 4C:
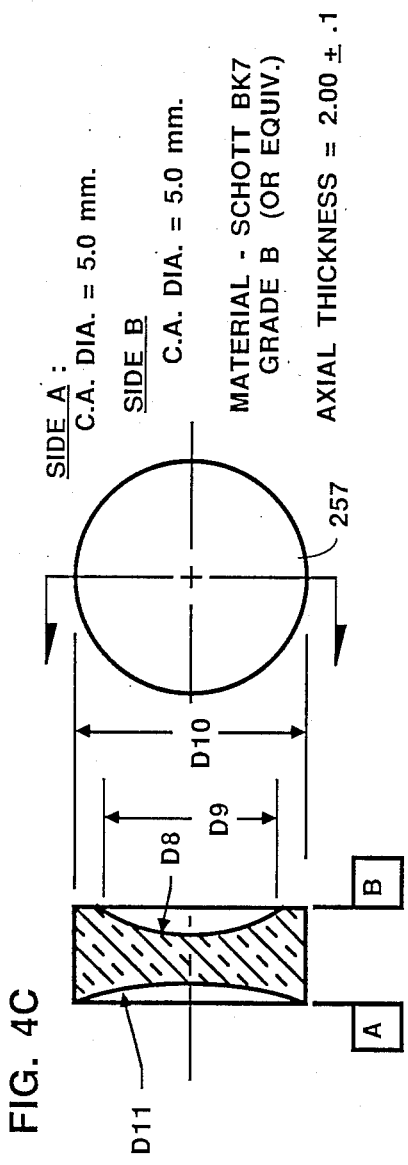
Figure 5A:
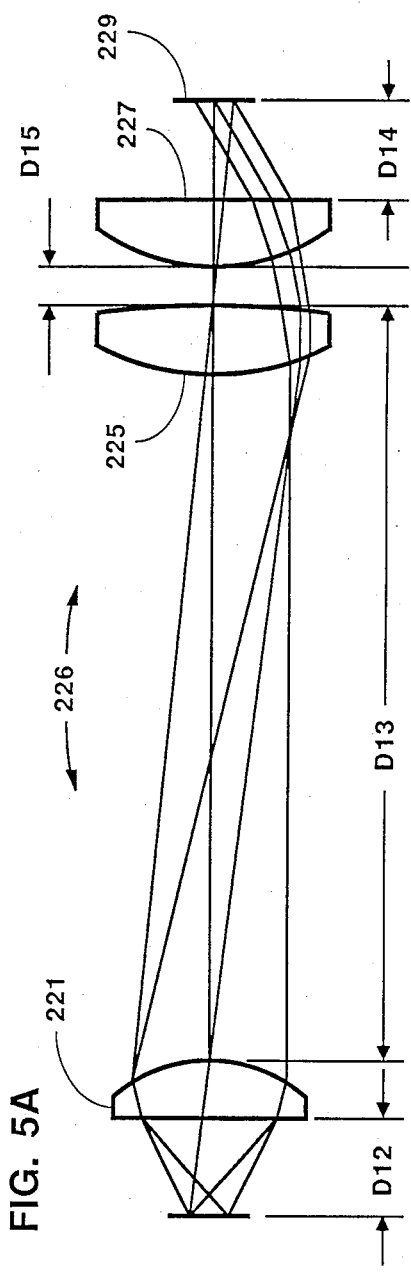
FIG. 5A illustrates a collector lens and Fabry lens group according to the invention.
Figure 5D:
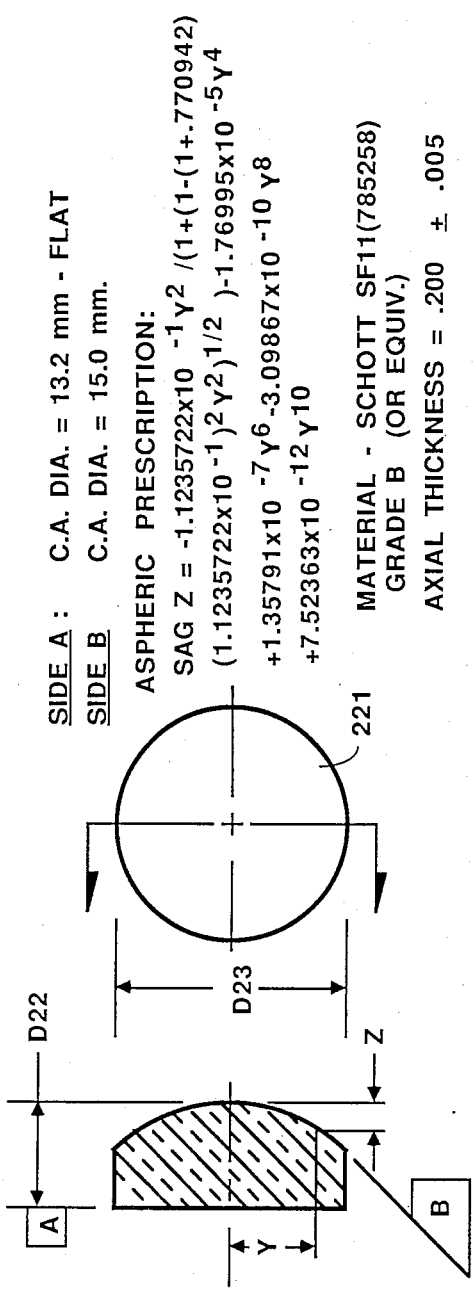

Shown in FIG. 1 and FIGS. 2A and 2B is a schematic representation of a preferred embodiment of the invention which is made up of an electrophoresis apparatus 100 having a polyacrylamide slab gel 104, a laser 300 for providing an intense source of electromagnetic radiation, and an optical detection system 200 that directs the laser light onto the slab gel and detects the fluorescence of dyes attached to the materials being electrophoresed in the gel. During operation, the electrophoresis apparatus 100, the laser 300 and the optical detection system are enclosed in a light-tight environment, such as a box (not shown).

The electrophoresis apparatus 100 has a transparent front panel 106 and a transparent back panel 105 with gel 104 sandwiched therebetween. Also included is lower buffer chamber 101 and an upper buffer chamber 109 which are designed to provide communication between the gel 104 and the buffer solutions contained in the two chambers. The buffer chambers and the plates 105 and 106 are held in a fixed relationship to each other by a frame 107 having clamps 113 and 115. The electrophoresis apparatus also includes a beam dump 111 for stopping direct light from laser 300 from traversing a path beyond the electrophoresis apparatus. In addition, each buffer chamber includes a banana plut (112 and 114) for connecting a voltage source across the gel (typically 1000–1500 volts). In one preferred mode, the gel 104 is 8% by weight of acrylamide monomer and is prepared according to techniques well known in the art (see Maniatis, et al, *Molecular Cloning*, page 478). In order to introduce samples to be sequenced into the electrophoresis apparatus, a series of wells such as 91 through 97 is created at the top of the gel as illustrated schematically in FIGS. 3A and 3B. First, spacers 98 and 99 are placed on plate 106 to define the desired thickness of the gel 104 and plate 105 is affixed to plate 106 creating a cavity therebetween. Typical materials for spacer 98 and 99 are nylon or Delrin ™ strips. The gel is then poured into the cavity, the comb is placed on top, and the gel is allowed to solidify. The comb 102 is then removed, leaving the series of wells at the top of the gel. Samples can then be injected directly into the wells. Because the samples are suitably segregated by the walls of the wells, and because the diffusion coefficient is very low in the gel, well defined lanes such as lanes 110 and 108 illustrated in FIG. 2A appear during electrophoresis, one lane for each well. Although only seven lanes have been shown, in the preferred mode sixteen are typically used for a 10-inch wide gel. The depth and width of the wells are both typically in the range of 0.5 cm to 1 cm, and spacers 98 and 99 are usually about 1 cm wide. Gel thickness is typically in the range of 0.5 mm to 1.0 mm, and the preferred height of the gel is 15.75 inches. The plates 105 and 106 are typically 3.0 mm to 5.0 mm thick and are constructed of a clear, non-fluorescent material such as pyrex borosilicate glass. A particularly suitable material is a Schott glass known in the art by the tradename TEMPAX ™ which has a low fluorescence, an index of refraction close to that of the gel (n=1.47), and which can withstand high temperatures and thermal shock. (TEMPAX ™ is produced by the Schott Optical Company.) It should also be noted that there is a cut-out 90 in the top of plate 106 in order for the buffer solution in buffer chamber 109 to communicate with the gel during electrophoresis. In another preferred mode, the top 2 cm to 4 cm of the gel immediately below the comb is poured with 5% by weight of acrylamide monomer, with the balance of the gel being 8% acrylamide monomer. This combination of concentrations appears to enhance the speed and the amount of the sample materials which enter the gel initially. Yet another approach is to mix agarose with the acrylamide gel in the top 2 cm to 4 cm.

As illustrated in FIG. 1, the electrophoresis apparatus is designed to fit onto a shelf 117 of an enclosure 370. The shelf is configured to slide into the enclosure 370 bringing the plate 106 into contact with a heat transfer plate 119, in order to equalize and dissipate heat generated during the electrophoresis process. A slot 123 in plate 119, permits light to pass through the plate 119 for causing fluorescence of the various dyes and for permitting detection of that fluorescence. The enclosure 370 includes a base plate 241 that is located above the shelf 117 so that the buffer chamber 101 can slide thereunder. Structural integrity of the enclosure is provided by liner 121 that fits around the perimeter of the electrophoresis apparatus 100 when it is in place on the shelf.

The optical detection system 200 is attached to a plate 239 which rides on a translational stage 231 attached to base plate 241 via a guide rail 233. The stage is translated horizontally back and forth by a screw 252 driven by a DC motor 237, and position of the stage is monitored by a shaft encoder 238. Optical sensors 242 and 244 (not shown) are used to monitor end of travel for the stage. Although there are several different translational stages that can be used, a particularly useful one because of its size and smooth operation is bearing track assembly part number RSR 5WUU, available from THK, Co. Ltd., located in Elk Grove Village, Ill.

As indicated earlier, the source of electromagnetic radiation to cause fluorescence is laser 300. In the preferred embodiment, an Argon ion laser is used which is operated in a mode providing two lines, one at 488.0 nanometers and one at 514.5 nanometers, with both lines having about equal power, about 7 mW for each line, and a total power of 20 mW. Unlike the optical detection system 200, laser 300 is held fixed. Light 250 emanating from the laser first impinges on a 45° mirror 253, then on a 45° mirror 251 so that it again becomes parallel to the direction of translation of the optical detection system. Thus, motion of the optical detection system does not effect the incidence angle of the light into the optical detection system.

The optical detection system 200 is made up of a focussing telescope 260 having lenses 257 and 259 to decrease the size of the incident beam and to focus the light onto the gel lanes. The path of the light from the focussing telescope is diverted toward the gel by a Brewster angle mirror 255 through a window 125, the window and the mirror being fixed relative to the stage 231. The incidence angle at mirror 255 was chosen at the Brewster angle in order to minimize the polarized laser light scatter that interferes with fluorescence detection. The individual lanes are accessed by moving the stage back and forth along guide rail 233. As light from laser 300 strikes a dye in a lane, the dye fluoresces as indicated for lane 108. A collector lens 221 collects a portion of the fluorescent light and directs it toward a filter wheel 223 which is made up of four color filters arranged as quadrants of the wheel. As the filter wheel is rotated, the pass bands of the filters selectively transmit particular wavelengths of the fluorescent light, one at a time, to a Fabry lens group 226, made up of lenses 225 and 227.

The Fabry group is located at the focus of the collector lens 221 and is configured to image the collector lens onto the active area of a side-on photomultiplier tube 229, such as an R928 available from Hamamatsu, rather than to image the lanes themselves. Generally, the photocathode output signal varies with the location of the light signal on the active area. By imaging the collector lens instead of the lanes, the location of the light on the photomultiplier is stable even when the location of illumination on the gel is changed. Hence, one does not see spurious variations in the photomultiplier output signal if the illumination location on the gel should be changed for some reason e.g. from imperfect alignment. Another purpose of using a pair of lenses for the Fabry group is to further desensitize the system to aberration components arising from alignment errors. In order to focus the collector lens onto the photomultiplier tube within a reasonable distance, the Fabry group must have a relatively high power. To use one lens to achieve high power results in field curvature and geometric distortion which, if not corrected, would cause the image on the active surface to move in and out of focus if the area of illumination varies laterally during a measurement sweep e.g. if it were not properly aligned or if the gel plate should have ripples. Hence, a two lens group is used, the Fabry lens 227 being an aspheric, so that together field curvature and geometric distortion are removed. Hence, even with misalignment or ripples, the image on the photomultiplier is exceedingly stable and does not change in size.

The particular color filters used with system vary with the selection of dyes. In the preferred mode, each dye is selected from a separate one of four sets of dyes. For those dyes, the filters chosen have nominal center wavelengths of 540 nm, 560 nm, 580 nm and 610 nm, all with a band pass of 10 nm (as measured at the 50% transmission point). Such filters are available, for example, from OMEGA Optical of Battlesborough, VT. The four sets of dyes are as follows. Set I consists of fluorescein mono-derivatized with a linking functionality at either the 5 or 6 carbon position (as determined by the Color Index numbering system). Illustrative examples of set I members include fluorescein-5-isothiocyanate,
fluorescein-6-isothiocyanate (the -5- and -6-forms being referred to collectively as FITC),
fluorescein-5-succinimidylcarboxylate,
fluorescein-6-succinimidylcarboxylate,
fluorescein-6-succinimidlylcarboxylate,
fluorescein-5-iodoacetamide,
fluorescein-6-iodoacetamide, fluorescein-5-maleimide, and fluorescein-6-maleimide.

These examples of members of set I are available commerically, e.g. Molecular Probes, Inc. (Junction City, OR), or can be synthesized using standard techniques. Set II consists of 2',7'-dimethoxy-4',5'-dichlorofluorescein mono-derivatized with a linking functionality at the 5 or 6 carbon position (the carbons being identified in accordance with the Color Index numbering system). Set II members can be obtained by standard modifications of 2,7-dimethoxy-4,5-dichloro-9-(2',4'-dicarboxylphenyl)-6-hydroxy-3H-xanthen-3-one and 2,7-dimethoxy-4,5-dichloro-9-(2',5'-dicarboxyphenyl)-6-hydroxy-3H-xanthen-3-one (IUPAC notation) disclosed in U.S. Pat. No. 4,318,846. For example, the 4' and 5' carboxys of these compounds can be condensed with N-hydroxysuccinimide using dicyclohexylcarbodiimide to form an amine-selective linking functionality, e.g. as illustrated by examples 6 and 8 of the above-referenced patent (Col. 28-29). Kasai et al., *Anal. Chem.*, Vol. 47, pgs. 34–37 (1975), discloses the basic technique for such condensations. Examples of members of Set II dyes are 2',7'-dimethoxy-4',5'-dichlorofluorescein-5-succinimidylcarboxylate and 2',7'-dimethoxy-4',5'-dichlorofluorescein-6-succinimidylcarboxylate (the -5- and -6- forms being referred to collectively as DDFCS). Set III consists of tetramethylrhodamine monoderivatized with a linking functionality at either the 5 or 6 carbon position. Illustrative examples of set III members include
tetramethylrhodamine-5-isothiocyanate,
tetramethylrhodamine-6-isothiocyanate (the -5- and -6- forms being referred to collectively as TMRITC),
tetramethylrhodamine-5-iodoacetamide,
tetramethylrhodamine-6-iodoacetamide,
tetramethylrhodamine-5-succinimidylcarboxylate,
tetramethylrhodamine-6-succinimidylcarboxylate,
tetramethylrhodamine-5-maleimide, and
tetramethylrhodamine-6-maleimide.

These exemplary dyes are available commercially, e.g. Molecular Probes, Inc., or can be synthesized using standard techniques. Set IV consits of rhodamine X derivatives having a disubstituted phenyl attached to the molecule's oxygen heterocycle, one of the substituents being a linking functionality attached to the 4' or 5' carbon (IUPAC numbering) of the phenyl, and the other being an acidic anionic group attached to the 2' carbon. Illustrative examples of set IV members include Texas Red (trademane of Molecular Probes, Inc.), rhodamine X-5-isothiocyanate, rhodamine X-6-isothiocyanate, rhodamine X-5-iodoacetamide, rhodamine X-6-iodoacetamide, rhodamine X-5-succinimidylcarboxylate, rhodamine X-6-succinimidylcarboxylate, rhodamine X-5-maleimide, and rhodamine X-6-maleimide. Most of these exemplary dyes are availabe commercially, e.g. Molecular Probes, Inc., or can be synthesized using standard techniques. For example, in the case of Texas Red it can be synthesized according to the procedure disclosed in Titus et al., "Texas Red, a Hydrophilic, Red-Emitting Fluorophore for Use with Fluorescein in Dual Parameter Flow Microfluorometric and Fluorescence Microscopic Studies," *J. Immunological Methods*, Vol. 50, pgs. 193–204 (1982).

The details of the optics assemblies making up the optical detection system are provided in FIGS. 4A through 4C and FIGS. 5A through 5C, which show the relative positions of the various lens elements and the specifications for the lenses. The lens dimensions are provided in a Table in FIG. 6.

Shown in FIGS. 7A through 7D are the mechanical details of the optical detection system 200. A housing 701 holds the focussing telescope 260, and the Brewster angle mirror 255, and contains the collector lens 221 and the slot 125. Light from the collector lens is directed down a tube 703 to the filter wheel 223 which is contained in a wheel housing 705. The Fabry group 226 is contained in a housing 707 adjacent the photomultiplier tube 229. A power supply 709 for the photomultiplier tube is located at one end of the tube and a circuit board 711 provides the electronic controls for the photomultiplier tube and the filter wheel. A stepper motor 713 is used to drive the filter wheel via a drive belt 716 entrained over pulleys 715 and 717, pulley 715 being used to drive shaft 714 which is connected to the filter wheel. An index wheel 719 is used to encode the filter wheel position via an optical encoder 721. FIG. 7E provides a Table having the relevant mechanical dimensions of the optical detection system 200.

Figure 8:
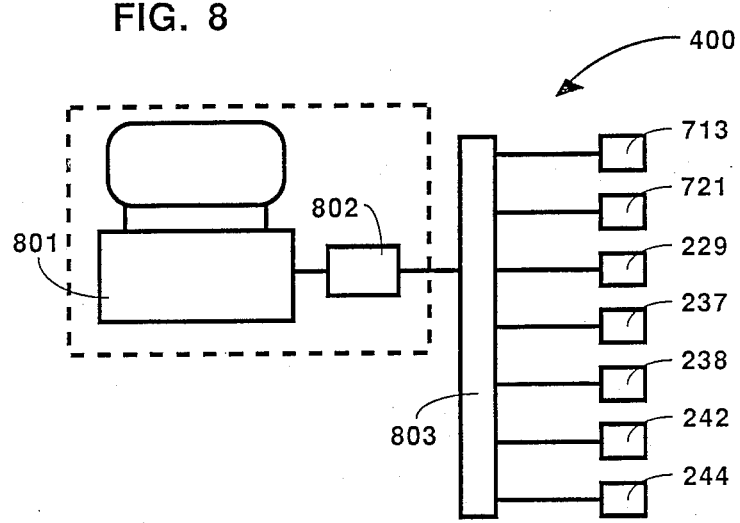
FIG. 8 is a schematic illustration of a computer system according to the invention.

Shown in FIG. 8 is a schematic representation of a computer system 400 for controlling operation of the optical detection system and for performing the required data analysis. The system 400 includes a central computer 801 such as an IBM pc which is coupled to a process control computer 802 such as the Z80 based microcomputer used by Applied Biosystems of Foster City, Calif., in their 381 DNA synthesizer. The process control computer 802 is coupled to an interface 803 for communicating with the elements of the optical system which require monitoring of control. Those elements include the stepper motor 713, the encoder 721 for the filter wheel, the output from the photomultiplier tube 229, the drive motor 237 for the stage 231, the shaft encoder 238 and the limit switches 242 and 244 for stage 231. Analysis of intensity information obtained during the sequencing process is performed by the central computer 801.

METHOD OF OPERATION

First, samples to be sequenced are prepared according to the Sanger enzymatic method described earlier in the Background of the Invention. The buffer chambers are filled with an appropriate buffer and the electrophoresis apparatus is loaded onto the sliding shelf 117. The gel is then pre-electrophoresed for about one-half hour to remove any fluorescent impurities. The samples are then injected into the wells at the top of the gel and a high voltage is connected between the buffer chambers to start the electrophoresis process.

To start the detection portion of the operation, the laser is turned on and the computer 801 indexes the filter wheel to a first filter and causes the stage 231 to move the optical detection system across the 16 vertical lanes of the gel 104. Each lane corresponds to a separate sequencing operation using all four dyes, in the same manner as the single column used by Lloyd Smith, et al. The stage is moved across the gel in about 1 second, and 192 light intensity measurements are made during the scan. Each measurement of the light intensity is an average taken over a distance of approximately 0.8 mm and over a time of 0.005 seconds, these measurements hereinafter referred to as channels. At the end of the first scan, the computer causes a second filter to be rotated into position (about 0.5 sec.) in the path of the light being detected. The direction of the stage 231 is then reversed and the optical detection system 200 resumes detection on this reverse scan, again measuring 192 channels. This process is then repeated for the third and fourth filters.

Figure 9:
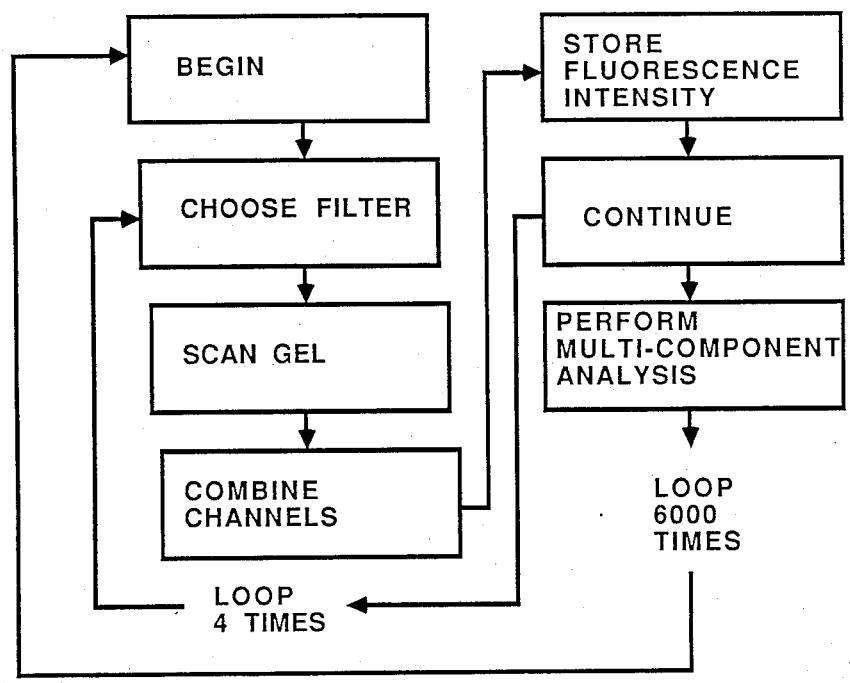
FIG. 9 is a flow chart illustrating the computer logic to arrive at a nucleic acid sequence from the electrophoresis and timing data.

In the preferred mode, each lane in the gel is designed to be about 4 mm wide, with each lane being separated by about 4 mm, as determined by the comb design when preparing the gel. With this design, each lane spans 5 channels. To increase signal to noise ratio, intensity data associated with the channels corresponding to a particular lane are summed. The four passes past a particular lane then provide four color data for that lane at that time. During each 6 second period (4 filters×(1 sec/scan+0.5 sec/filter change), a four color datum point is recorded for each lane. This four color data can then be analyzed using multicomponent analysis to provide the desired sequence information as will be described later. A flow chart illustrating the above method is shown in FIG. 9.

Compared to the speed at which the sample DNA moves down a lane, the six second time required to obtain the four color data is nearly simultaneous. In effect, a four wavelength emission spectrum is measured for each time unit during the electrophoresis at a fixed distance down the gel. By multicomponent analysis, the data for these four wavelengths yields information about the four relative concentrations of the dye-labeled DNA pieces moving down a lane. Peak concentrations of a particular dye label then correspond to a particular base in the DNA sequence. The four plots of concentration versus time, are overlayed and the peaks determined, the matching of the peaks with the DNA bases yeilding the sequence.

Analytically, the multicomponent analysis amounts to solving four equations in four unknowns. The general formula for the analysis is:

$$\sum_{j=1}^{4} A_{ij} C_j = F_i \quad i = 1, 2, 3, 4$$

where Aij is the standard fluorescence of dye j at filter wavelength i, and Cj is the concentration of dye j, Fi is the fluorescence intensity measured through filter i. Solving the above equations yields a unique set of concentrations at each point in time. For completely automated analysis, standard noise reduction and peak finding algorithms can be used to call the sequence, or a trained individual can inspect the set of concentrations to arrive at a sequence. For convenience during operation, the four components of concentration are plotted simultaneously on a color monitor on computer system 801 while the gel is being scanned during electrophoresis.

The standard fluorescence coefficients Cij are determined by measuring the fluorescence with each filter when a known unit concentration of each dye is present in the gel, one dye at a time. For such measurements, one can use a single band of dye-labelled primer. Generally these coefficients are a function of the laser wavelength and intensity, the gel characteristics, the optical filter, and photomultiplier response.

UTILITY OF THE INVENTION

Figure 10:
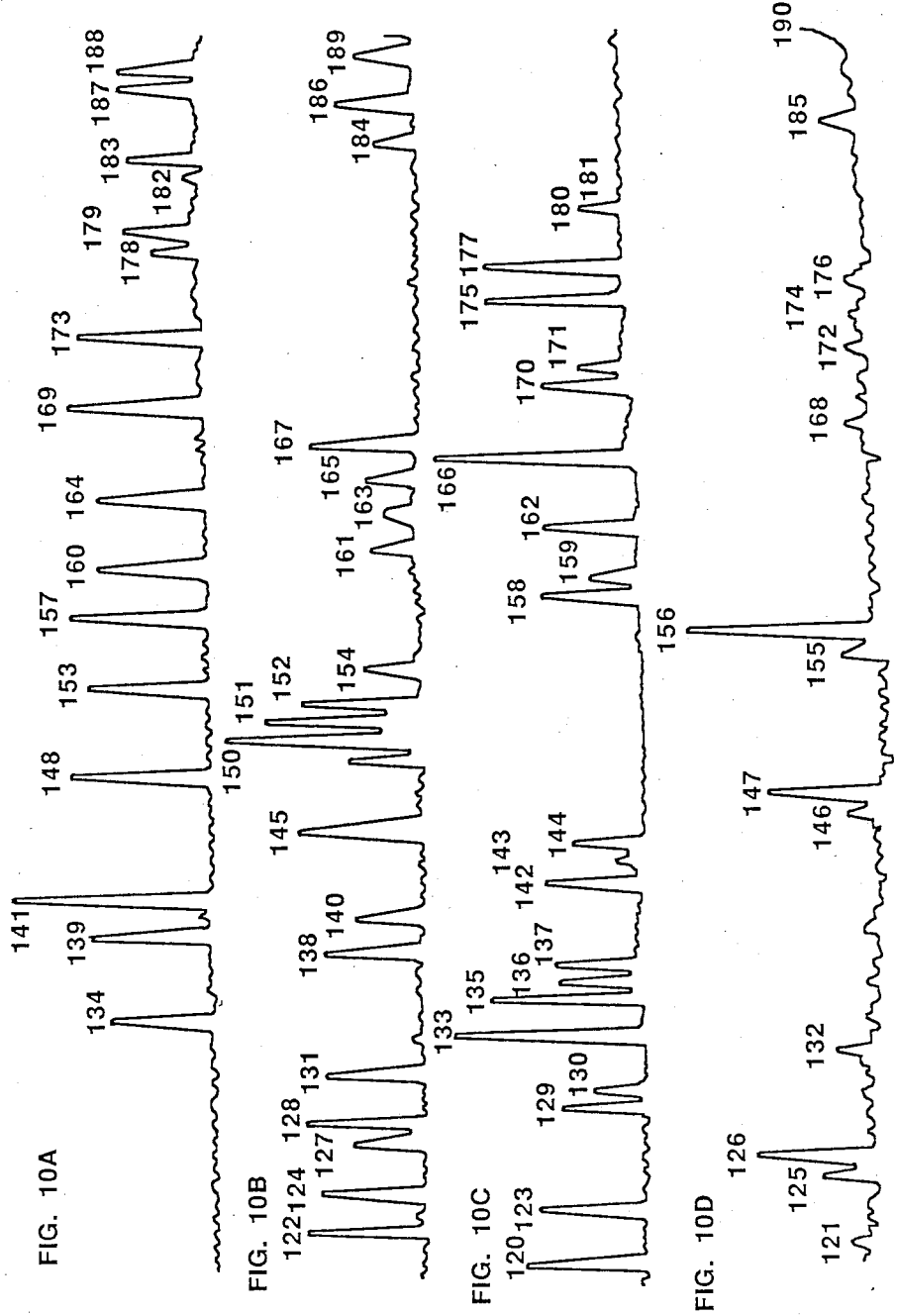
FIGS. 10A–10D are plots of intensity data taken with the apparatus of the invention for each of four wavelengths.
Figure 11:
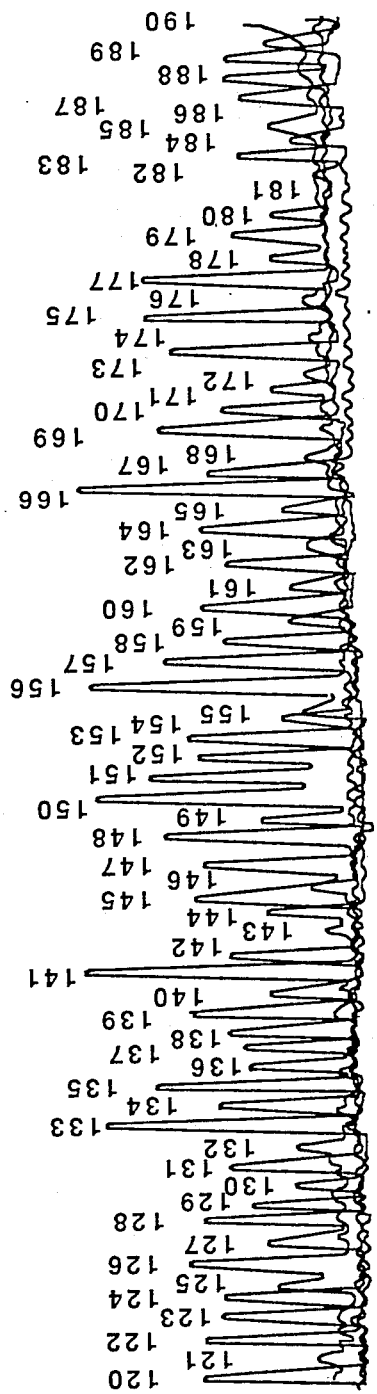
FIG. 11 is a superposition of the plots of FIGS. 10A–10D.

FIGS. 10 and 11 illustrate the result of a DNA sequencing run made with the invention on bases 120 through 190 of the cloning vector mp8 of the bacteriohpage M13 using DNA polymerase, Klenow fragment. The results shown correspond to one lane of the sixteen, the other lanes providing the same kind of information for the particular samples sequenced there. The specific dyes corresponding to this run are fluorescein-5-isothiocyanate; 2',7'-dimethoxy-4'-5'-dichlorofluorescein; tetramethylrhodamine-5-isothiocyanate, and Texas Red. FIG. 10 shows the relative intensities recorded for each base during sequencing run as a function of time. FIG. 11 shows the four different intensities plotted one on top of the other, which makes the sequence somewhat easier to call, since the relationship between peaks becomes more apparent. This relationship is even clearer when using a color monitor on the computer 801 so that the intensity for each base is plotted in a different color, one on top of the other. As indicated, in most instances, the call is unequivocal. However, certain low signal peaks do occur. For example, see bases 174 and 181. In an unknown sample, such bases in the sequence might be overlooked. However, as is typical even in radiographic sequencing, those skilled in the art often do more than one sequencing run, typically with other sequencing emzymes to eliminate ambiguous base calls caused by the particular chemistry chosen. For example, it is well known to those skilled in the art that the cytosine sequence has large variations in amplitude. Hence, one typically also performs a sequencing run on the complementary strand to check the results of the cytosine call. Another approach is to use a different enzyme completely, for example, reverse transcriptase.

Hence, the automated method and apparatus of the invention can be used to provide high speed, definitive sequencing analysis on many samples at once. This permits more than one clone to be sequenced at a time, vastly decreasing the time required to sequence larger fragments, and reducing costs accordingly. In addition, as designed, once the system is constructed, little if any further alignment by trained personnel is required at the operating end. Further, as compared to the radiographic method, the real time sequencing method has many other benefits. First, sequencing is performed with all four bases in one lane, rather than four separate lanes, thus avoiding mobility variation problems between lanes. Second, no radioactive materials are required, and the materils that are used have a considerably longer shelf life than radioactive materials. Third, because the system is real time, a run can be stopped in the middle and redone, rather than having to wait for the entire radiographic sequencing to be concluded, only to find out the run was bad.

Those skilled in the art will understand that there are many variations of the above apparatus and method that fall within the purview of the invention. For example, one could use a series of independent columns arranged in a linear array for the electrophoresis lanes rather than a slab gel. Also, different percentage gels could be used for the entire slab or different percentage gels could be used in adjacent lanes of the slab, in order to separate different size fragments, in a manner similar to the stacking gels used in protein electrophoresis. Furthermore, different stages and drive systems could be used as well as different sources of electromagnetic radiation.

We claim:

1. An apparatus for detecting electromagnetic radiation from a plurality of lanes in an electrophoresis system wherein said plurality of lanes are arranged in a planar array comprising:
   optical means for detecting said radiation at a plurality of wavelengths emanating from said plurality of lanes, comprising:
      collecting means for collecting and focussing said radiation;
      filter means for receiving said radiation from said collecting means and for selectively transmitting said plurality of wavelengths of said radiation received from said collecting means;
      detection means for measuring intensity of radiation received from said filter means;
   stage means for mounting said optical means, and for translating said optical means in a direction parallel to said planar array in order to move said collecting means to receive radiation from said lanes, one lane at a time;
   computer means coupled to said filter means and said stage means for controlling said filter means and said stage means, for receiving intensity data from said detection means, and for correlating said intensity data with corresponding lanes of said electrophoresis system and corresponding wavelengths transmitted by said filter means.

2. An apparatus as in claim 1 further comprising:

source means for providing said electromagnetic radiation and for directing said radiation in a direction parallel to said planar array;

and where said optical means further comprises deflection means fixed relative to said stage means for deflecting said radiation away from said direction parallel to said planar array and towards said planar array.

3. An apparatus for determining the base sequences of nucleic acids, wherein said nucleic acids have been fragmented and the fragments labelled with four different dyes that fluoresce at four different wavelengths, each dye being attached to fragments terminating at a different one of A, G, T, or C, comprising:

source means for providing electromagnetic radiation in a first direction;

electrophoresis means constructed to have a plurality of lanes, said lanes arranged in a line parallel to said first direction, with each lane having a side constrained by a material transparent to radiation from said source means, for electrophoresing said nucleic acids simultaneously in said plurality of lanes;

a radiation detection system comprising:

deflection means for deflecting said radiation from said source means toward said line of lanes in a direction incident on said transparent material;

collection means for collecting light fluorescing from said lanes in response to receiving radiation from said source means;

filter means for selectively transmitting four bands of wavelengths of radiation received from said collection means, one band at a time, each band corresponding to a different dye in the set of four dyes;

detector means for receiving radiation transmitted by said filter means and for providing a signal functionally related to intensity of the radiation received;

stage means for holding said radiation detection system and for translating said radiation detection system back and forth across said plurality of lanes in a direction parallel to said line of lanes while said nucleic acids are being electrophoresed; and computer means for controlling the radiation detection system and for analyzing signals from the detector means to detemine a time ordered sequence of said dyes traversing each of said lanes during electrophoresis.

4. A method of detecting fluorescence from multiple lanes of an electrophoresis apparatus comprising:

illuminating molecules in said lanes with electromagnetic radiation, said molecules having fluorescent dyes attached thereto, said molecules moving through said lanes by electrophoresis;

collecting light resulting from fluorescence of said dyes, by moving a collecting lens across said lanes during electrophoresis;

focussing said collected light on an intensity sensitive apparatus moving with said collecting lens to provide an intensity profile as said collecting lens is moved across said lanes; and sorting said intensity profile in time to identify a time ordered sequence of dyes traversing each of said lanes.

5. An electrophoresis apparatus comprising:

means for providing a plurality of substantially parallel electrophoretic lanes along which fluorescently labeled samples migrate, said electrophoretic lanes being substantially disposed in a plane;

electrodes disposed at opposite ends of said electrophoretic lanes;

a power source coupled to said electrodes for driving said samples along said electrophoretic lanes;

source means for providing a beam of electromagnetic radiation;

deflection means for deflecting said beam of electromagnetic radiation toward said lanes, one lane at a time, said deflected beam having a directional component orthogonal to said plane as said deflected beam traverses each lane;

detector means for detecting radiation fluorescing from said lanes in response to receiving radiation from said source means, and for providing a signal functionally related to the intensity of the radiation received;

computer means coupled to said detector means and to said deflection means for analyzing said signal from said detector means to determine a time ordered sequence of said samples traversing each of said lanes during electrophoresis.

6. Apparatus as in claim 5 further comprising collection means for increasing the proportion of fluorescent radiation that impinges on said detector means.

7. Apparatus as in claim 5 wherein said deflection means comprises a mirror means for deflecting said beam toward said plane and a stage means for mounting said mirror, said stage means for translating said mirror means in a direction parallel to said planar array.

8. Apparatus as in claim 7 further comprising collection means for increasing the proportion of fluorescent radiation that impinges on said detector means.

9. Apparatus as in claim 8 wherein said stage means is coupled to said collection means and to said detector means for translating said collection means and said detector means as said stage means translates said mirror means.

10. An electrophoretic fluorescence detection apparatus comprising:

source means for providing electromagnetic radiation;

electrophoresis means constructed to have a plurality of lanes, said lanes arranged in a line parallel to a first direction, with each lane having a side constrained by a material transparent to radiation from said source means, for electrophoresing fluorescently labeled samples simultaneously in said plurality of lanes;

deflection means for directing said electromagnetic radiation onto said lanes, a single lane at a time;

a radiation detection system comprising:

filter means for selectively transmitting a plurality of bands of wavelenghts of radiation of fluorescing from said lanes in response to receiving radiation from said source means;

detector means for receiving said radiation transmitted by said filter means and for providing a signal functionally related to intensity of the radiation received;

computer means coupled to said deflection means and to said radiation detection system for controlling said detection system and for analyzing said signal from the detector means to determine a time ordered sequence of the samples traversing each of said lanes during electrophoresis.

11. Apparatus as in claim 10 wherein said radiation detection system further comprises collection means for increasing the proportion of fluorescent radiation that impinges on said detector means.

12. Apparatus as in claim 11 wherein said deflection means comprises translation means coupled to said computer means for moving said deflection means parallel to said first direction lanes, said translation means also including mounting means for mounting said radiation detection system thereto, so that said radiation detection system is also translated parallel to said lanes.

13. An apparatus for determining the base sequences of nucleic acids, wherein said nucleic acids have been fragmented and the fragments labelled with four different dyes that fluoresce at four different wavelengths, each dye being attached to fragments terminating in a different one of A, G, T, or C, comprising:

source means for providing electromagnetic radiation;

electrophoresis means constructed to have a plurality of lanes, said lanes arranged in a line parallel to a first direction, with each lane having a side constrained by a material transparent to radiation from said source means, for electrophoresing the fluorescently labeled fragments simultaneously in said plurality of lanes;

deflection means for directing said elecromagnetic radiation onto said lanes, a single lane at a time;

a radiation detection system comprising:

filter means for selectively transmitting four bands of wavelengths of radiation fluorescing from the fragments being electrophoresed in said lanes in response to receiving radiation from said source means, said bands corresponding to the four wavelengths of said dyes;

detector means for receiving radiation transmitted by said filter means and for providing a signal functionally related to intensity of the radiation received;

computer means coupled to said deflection means and to said detection system for controlling said deflection means and for analyzing signals from the detector means to determine a time ordered sequence of the fragments traversing each of said lanes during electrophoresis.

14. An apparatus as in claim 13 wherein said radiation detection system further comprises collection means for increasing the proportion of fluorescent radiation that impinges on said detector means.

* * * * *